(12) United States Patent
Fan

(10) Patent No.: US 9,597,377 B2
(45) Date of Patent: Mar. 21, 2017

(54) STABLE FORMULATIONS OF PURIFIED PROTEINS

(75) Inventor: Jian-Qiang Fan, Demarest, NJ (US)

(73) Assignee: MOUNT SINAI SCHOOL OF MEDICINE OF NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 11/317,404

(22) Filed: Dec. 23, 2005

(65) Prior Publication Data

US 2006/0153829 A1 Jul. 13, 2006

Related U.S. Application Data

(63) Continuation of application No. 10/771,236, filed on Feb. 2, 2004, now abandoned.

(60) Provisional application No. 60/444,136, filed on Jan. 31, 2003.

(51) Int. Cl.
| | |
|---|---|
| A61K 38/47 | (2006.01) |
| A61K 31/445 | (2006.01) |
| A61K 31/46 | (2006.01) |
| A61K 9/00 | (2006.01) |

(52) U.S. Cl.
CPC ............ *A61K 38/47* (2013.01); *A61K 31/445* (2013.01); *A61K 31/46* (2013.01); *A61K 9/0019* (2013.01)

(58) Field of Classification Search
CPC ...... C12N 9/2402; C12N 9/2465; C12N 9/96; C07K 14/47; C12Y 302/01022; A61K 45/06; C07D 405/12; C07C 215/76; C07C 279/12; C07H 21/02
See application file for complete search history.

(56) References Cited

U.S. PATENT DOCUMENTS

| | | | |
|---|---|---|---|
| 3,607,858 A | 9/1971 | Querry | |
| 5,030,638 A | 7/1991 | Partis et al. | |
| 5,179,023 A * | 1/1993 | Calhoun et al. | 435/235.1 |
| 5,300,659 A * | 4/1994 | Fleet et al. | 548/556 |
| 5,472,969 A | 12/1995 | Platt et al. | |
| 5,580,884 A | 12/1996 | Platt et al. | |
| 5,798,366 A * | 8/1998 | Platt et al. | 514/315 |
| 5,801,185 A | 9/1998 | Platt et al. | |
| 6,051,598 A | 4/2000 | Shayman et al. | |
| 6,066,626 A * | 5/2000 | Yew et al. | 514/44 R |
| 6,200,812 B1 | 3/2001 | Pati et al. | |
| 6,255,113 B1 | 7/2001 | Zarling et al. | |
| 6,274,597 B1 | 8/2001 | Fan et al. | |
| 6,589,964 B2 | 7/2003 | Fan et al. | |
| 6,599,919 B2 | 7/2003 | Fan et al. | |
| 6,696,059 B2 | 2/2004 | Jacob et al. | |
| 6,774,135 B2 | 8/2004 | Fan et al. | |
| 2002/0013953 A1 | 1/2002 | Reuser et al. | |
| 2002/0035072 A1 | 3/2002 | Fan et al. | |
| 2002/0102329 A1* | 8/2002 | Lanahan et al. | 426/46 |
| 2002/0127213 A1 | 9/2002 | Jacob et al. | |
| 2003/0119874 A1 | 6/2003 | Fan et al. | |
| 2004/0204379 A1 | 10/2004 | Cheng et al. | |

FOREIGN PATENT DOCUMENTS

| | | |
|---|---|---|
| EP | 2441467 | 4/2012 |
| EP | 2444102 | 4/2012 |
| JP | 2002-531581 A | 9/2002 |
| JP | 2006-516645 | 7/2006 |
| JP | 2012-107020 | 6/2012 |
| WO | WO 99/62517 | 12/1999 |
| WO | 00/34451 | 6/2000 |
| WO | WO 01/07078 A1 | 2/2001 |
| WO | WO 01/97829 | 12/2001 |
| WO | WO2004/037373 | 5/2004 |
| WO | 2004/069190 | 8/2004 |
| WO | WO/2005/077093 | 8/2005 |
| WO | WO/2006/125141 | 11/2006 |
| WO | WO/2008/134628 | 11/2008 |

OTHER PUBLICATIONS

"Sodium citrate and citric acid solution." in: Gennaro, A., ed., Remington: The Science and Practice of Pharmacy, vol. II. 19th edition. (Easton, PA, Mack Publishing Co., 1995), pp. 932-933. RS91 .R45.*
Carpenter JF et al. 1993. Separation of freezing- and drying-induced denaturation of lyophilized proteins using stress-specific stabilization: I. Enzyme activity and calorimetric studies. Arch Biochem Biophys 303: 456-464.*
Merriam-Webster Online Dictionary definition of "tolerable." Accessed online May 12, 2008. <URL://www.merriam-webster.com/dictionary/tolerable>.*
Beck M. 2002. Agalsidase alfa—a preparation for enzyme replacement therapy in Anderson-Fabry disease. Expert Opin Investig Drugs 11: 851-858.*
Fan J-Q et al. 1999. Accelerated transport and maturation of lysosomal alpha-galactosidase A in Fabry lymphoblasts by an enzyme inhibitor. Nat Med 5: 112-115.*
Kato H et al. 1992. Fabry's disease. Int Med 31: 682-685.*
Kaushik JK et al. 1998. Thermal stability of proteins in aqueous polyol solutions: Role of the surface tension of water in the stabilizing effect of polyols. J Phys Chem B 102: 7058-7066.*
Fan J-Q et al. 2007. Active site-specific chaperone therapy for Fabry disease: Yin and yang of enzyme inhibitors. FEBS J 274: 4962-4971.*
Asano N et al. 2000. In vitro inhibition and intracellular enhancement of lysosomal a-galactosidase A activity in Fabry lymphoblasts by 1-deoxygalactonojirimycin and its derivatives. Eur J Biochem 267: 4179-4186.*
Ishii S et al. 1993. Characterization of a mutant alpha-galactosidase gene product for the late-onset cardiac form of Fabry disease. Biochem Biophys Res Comm 197: 1585-1589.*
Sawkar et al., Chemical Chaperones Increase the Cellular Activity of N370S B-glucosidase: A Therapeutic Strategy for Gaucher Disease; PNAS. 2002. 99: 15428-33.

(Continued)

*Primary Examiner* — Allison Fox

(74) *Attorney, Agent, or Firm* — Oblon, McClelland, Maier & Neustadt, L.L.P.

(57) ABSTRACT

This application provides methods of improving protein replacement therapy by combining protein replacement therapy with active site-specific chaperones (ASSC) to increase the stability and efficiency of the protein being administered. The application further provides stable compositions comprising the purified protein and an ASSC, and methods of treatment by administering the compositions.

4 Claims, 1 Drawing Sheet

(56) References Cited

OTHER PUBLICATIONS

Fan, "A contradictory treatment for lysosomal storage disorders: inhibitors enhance mutant enzyme activity," Trends Pharmacol Sci. Jul. 2003;24(7):355-60.
Ferrari et al., "Barriers to and new approaches for gene therapy and gene delivery in cystic fibrosis," Adv Drug Deliv Rev. Dec. 5, 2002;54(11):1373-93.
Hendricks et al., "Use of Human Mesenchymal Stem Cells as Gene Delivery Vehicles for the Treatment of Fabry's Disease," Blood 96 (11 part 1): 845a, 2000.
Romano et al., "Latest developments in gene transfer technology: achievements, perspectives, and controversies over therapeutic applications," Stem Cells. 2000;18(1):19-39.
Somia et al., "Gene therapy: trials and tribulations," Nat Rev Genet. Nov. 2000;1(2):91-9.
Boucher, "Status of gene therapy for cystic fibrosis lung disease," J Clin Invest. Feb. 1999;103(4):441-5.
Anderson, "Human gene therapy," Nature. Apr. 30, 1998;392(6679 Suppl):25-30.
Davies et al., "Prospects for gene therapy for cystic fibrosis," Mol Med Today. Jul. 1998;4(7):292-9.
Rosenecker et al., "Towards gene therapy of cystic fibrosis," Eur J Med Res. Mar. 23, 1998;3(3):149-56.
Alton, "Gene therapy: the case for cystic fibrosis," J R Soc Med. 1997;90 Suppl 31:43-6.
Verma et al., "Gene therapy—promises, problems and prospects," Nature. Sep. 18, 1997;389(6648):239-42.
Boucher, "Current status of CF gene therapy," Trends Genet. Mar. 1996;12(3):81-4.
Rosenfeld et al., "Parents' evaluations of wheezing in their children with asthma," Chest. Jan. 1996;109(1):91-3.
Wilson, "Gene therapy for cystic fibrosis: challenges and future directions," J Clin Invest. Dec. 1995;96(6):2547-54.
Priestman et al., Imino sugar therapy for type 1 Gaucher disease. Glycobiology. 2000; 11: iv-vi.
Ruvinov et al., Monovalent Cations Partially Repair a Conformational Defect in a Mutant Tryptophan Synthase α2β2 Complex (β-E109A); J. Biol. Chem. 1995; 270: 17333-38.
Morello et al., 2000, "Pharmacological chaperones: a new twist on receptor folding." Trends Pharmacol Sci., 21(12):466-469.
Rigat et al., 2003, "Evaluation of NAG-Thiazoline in mice: A chemical chaperone for the treatment of adult Tay-Sachs and Sandhoff diseases." Molecular & Cellular Proteomics, 2(9):848.
Eng, C.M. et al., 2001., "Safety and efficacy of recombinant human alpha-galactosidase A—replacement therapy in Fabry's disease." N Engl J Med 345: 9-16.
Saunier, B. et al., 1982, "Inhibition of oligosaccharide formation by 1-deoxynojirimycin, an inhibitor of processing glucosidases." L Bioi Chem 257: 14155-14161.
U.S. Appl. No. 11/607,286, Aug. 2, 2010 Amendment and Request for Continued Examination (RCE).
U.S. Appl. No. 11/607,286, Mar. 31, 2010 Final Office Action.
U.S. Appl. No. 11/607,286, Dec. 29, 2009 Response to Non-Final Office Action.
U.S. Appl. No. 11/607,286, Jul. 29, 2009 Non-Final Office Action.
U.S. Appl. No. 10/771,236, Mar. 17, 2006 Notice of Abandonment.
U.S. Appl. No. 10/771,236, Nov. 15, 2005 Advisory Action.
U.S. Appl. No. 10/771,236, Oct. 28, 2005 Response to Final Office Action.
U.S. Appl. No. 10/771,236, Jun. 27, 2005 Final Office Action.
U.S. Appl. No. 10/771,236, May 31, 2005 Response to Non-Final Office Action.
U.S. Appl. No. 10/771,236, Mar. 1, 2005 Non-Final Office Action.
European Search Report for EP application No. EP 11006495, dated Mar. 22, 2012.
European Search Report for EP application No. EP 11006504, dated Mar. 19, 2012.
Asano et al., "Sugar-mimic glycosidase inhibitors: natural occurrence, biological activity and prospects for therapeutic application", Tetrahedron: Asymmetry, 11(48): 1645-1680, 2000. Available online Aug. 29, 2000.
Lieberman et al., "Effects of pH and Iminosugar Pharmacological Chaperones on Lysosomal Glucosidase Structure and Stability", Biochemistry, 48(22): 4816-4827, 2009. Available online Apr. 20, 2009.
Okumiya et al., "Chemical chaperones improve transport and enhance stability of mutant α-glucosidase in glycogen storage disease type II", Molecular Genetics and Metabolism, 90(1):49-57, 2007. Available online Nov. 13, 2006.
Sun et al., "Ex Vivo and in Vivo Effects of Isofagomine on Acid β-Glucosidase Variants and Substrate Levels in Gaucher Disease", The Journal of Biological Chemistry, 287(6):4275-4287, 2012. Available online Dec. 13, 2011.
Japanese Office Action issued Jun. 25, 2013 in Patent Application No. 2012-000270 with English Translation.
Japanese Office Action issued Jun. 25, 2013 in Patent Application No. 2012-000271 with English Translation.
Office Action issued Nov. 5, 2013 in Chinese Patent Application No. 201210032893.9 (with English language translation).
Office Action issued May 13, 2013 in European Application No. 11 006 504.2.
Office Action issued May 13, 2013 in European Application No. 11 006 495.3.
Office Action issued Jan. 3, 2014 in Chinese Patent Application No. 201210033102.4 (with English language translation).
Office Action issued Mar. 13, 2014 in Israel Patent Application No. 214440 (with English language translation).
Office Action issued Mar. 9, 2014, in Israeli Patent Application No. 169562.
Office Action issued Oct. 17, 2013, in Canadian Patent Application No. 2,514,642.
Office Action issued Mar. 18, 2014 in Japanese Application No. 2012-000271 (With English Translation).
Office Action issued Mar. 18, 2014 in Japanese Application No. 2012-000270 (With English Translation).
Communication pursuant to Article 94(3) EPC issued May 9, 2014 in European Patent Application No. 10 011 598.9.
Office Action issued Feb. 4, 2014 in European Patent Application No. 04 707 422.4.
Examination Report as received in the corresponding India Patent Application No. 4070/delnp/2010 dated Aug. 27, 2014.
Office Action received in the corresponding Chinese Patent Application No. 201210033102.4 dated Sep. 18, 2014 w/English Translation.
Office Action as received in the corresponding Canadian Patent Application No. 2,814,774 dated Mar. 20, 2014.
Office Action as received in the corresponding European Patent Application No. 11 006 495.3-1402 dated Jun. 3, 2014.
Decision on Rejection as received in the China Patent Application No. 201210033099.6 dated Aug. 21, 2014 w/English Translation.
Third Office Action as received in the corresponding Mexican Patent Application No. MX/a/2008/012572 dated Jul. 31, 2014 w/partial English Translation.
Third Office Action received in the corresponding Chinese Patent Application No. 201210032893.9 dated Jul. 21, 2014 w/English Translation.
Jian-Qiang Fan, et al., "Accelerated transport and maturation of lysosomal α-galactosidase A in Fabry lymphoblasts by an enzyme inhibitor", Nature Medicine, vol. 5, No. 1, Jan. 1999, pp. 112-115.
Office Action as received in the corresponding Canadian Patent Application No. 2,814,774 dated Dec. 3, 2014.
Office Action received in the corresponding Canadian Patent Application No. 2,814,767 dated Dec. 1, 2014.
Office Action as received in the corresponding China Application No. 201210033102.4 dated Mar. 26, 2015 w/English Translation.
Office Action as received in the corresponding Japanese Patent Application No. 2012-271 dated Aug. 11, 2015, Appeal No. 2014-13855.

(56) References Cited

OTHER PUBLICATIONS

Anu R. Sawkar, et al., "Chemical chaperones increase the cellular activity of N370S β-glucosidase: A therapeutic strategy for Gaucher disease", PNAS, Nov. 26, 2002, vol. 99, No. 24.
Office Action as received in the corresponding Israel Patent Application No. 241315 dated Apr. 20, 2016 w/partial English translation.
Office Action as received in the corresponding Japanese Patent Application No. 2015-220246 dated Sep. 13, 2016 w/English Translation.
Jan-Qiang Fan, et al., "Accelerated transport and maturation of lysosomal α-galactosidase A in Fabry lymphoblasts by an enzyme inhibitor", Nature Medicine, vol. 5, No. 1, Jan. 1999, pp. 2-5.
Office Action issued Sep. 28, 2015 in Chinese Patent Application No. 201210033102.4 (with English translation).

\* cited by examiner

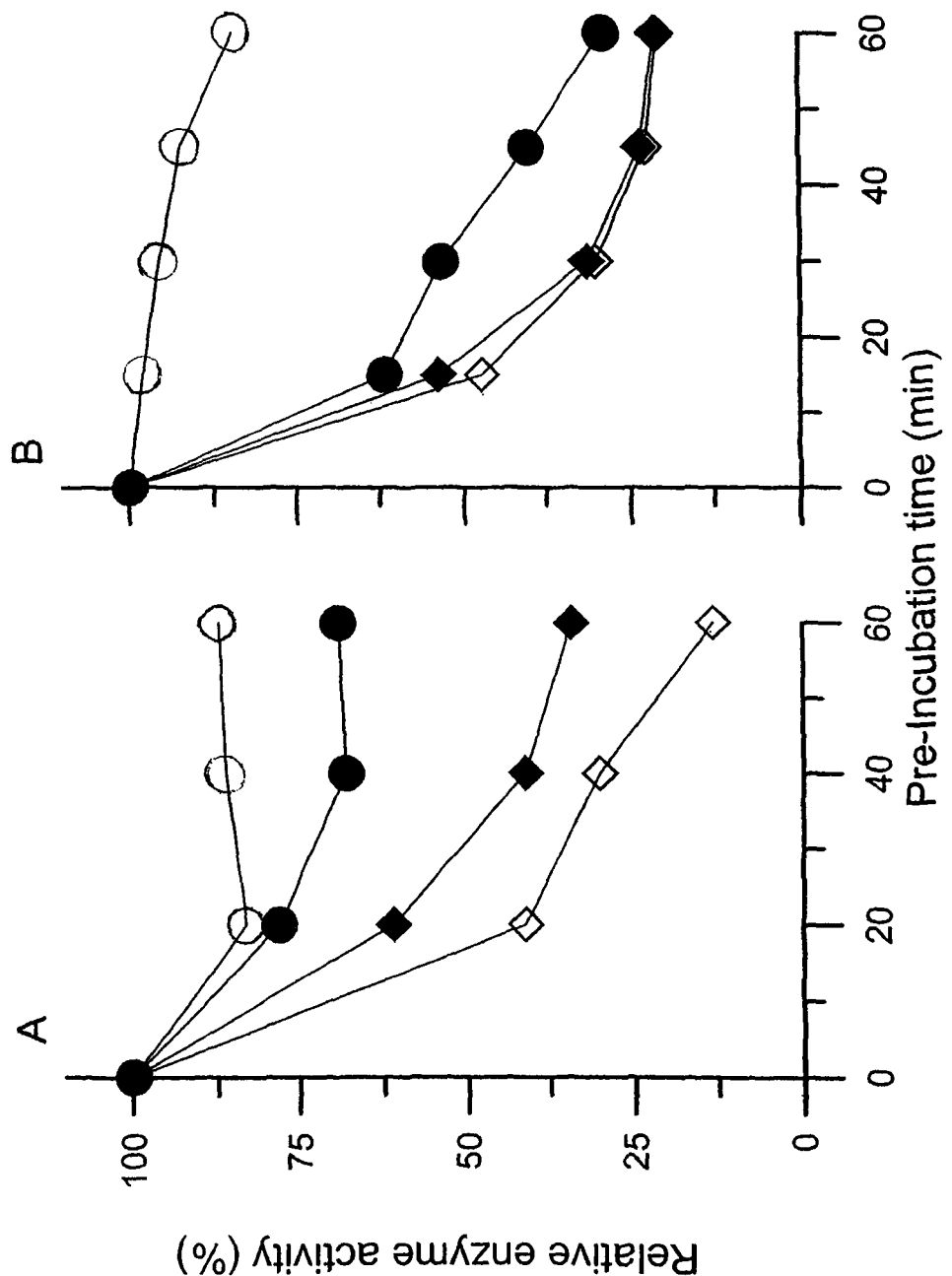

STABLE FORMULATIONS OF PURIFIED PROTEINS

This application is a continuation of U.S. patent application Ser. No. 10/771,236, filed on Feb. 2, 2004, which claims priority from U.S. Provisional Application Ser. No. 60/444,136, filed Jan. 31, 2003, the disclosures of which are herein incorporated by reference in their entirety.

FIELD OF THE INVENTION

This application provides methods of improving protein replacement therapy by combining protein replacement therapy with active site-specific chaperones (ASSC) to increase the stability and efficiency of the protein being administered. The application further provides compositions comprising the purified protein and an ASSC.

BACKGROUND

Protein Deficiency

Proteins are synthesized intracellularly according to the genomic nucleotide sequence of a particular gene through transcription, translation, and other processes. Protein deficiency can be caused by a mutation in the coding gene, which results in (i) non-synthesis of the protein; (ii) synthesis of the protein which lacks biological activity; or (iii) synthesis of the protein containing normal or partial biological activity, but which cannot be appropriately processed to reach the native compartment of the protein. Protein deficiency disorders that result from genetic mutations are also referred to as genetic disorders.

In addition to protein deficiencies resulting from genetic mutations, some protein deficiencies arise due to a disease, or as a side effect of a treatment for a disease (e.g., chemotherapy) or as a result of nutritional insufficiency.

Current Therapies.

There are numerous disorders resulting from protein deficiencies, some of which result from mutated, misfolded proteins (conformational disorders-see infra). One current therapy for treating protein deficiencies is protein replacement therapy, which typically involves intravenous, subcutaneous or intramuscular infusion of a purified form of the corresponding wild-type protein, or implantation of the protein in a bio-erodable solid form for extended-release. One of the main complications with protein replacement therapy is attainment and maintenance of therapeutically effective amounts of protein due to rapid degradation of the infused protein. The current approach to overcome this problem is to perform numerous costly high dose infusions.

Protein replacement therapy has several additional caveats, such as difficulties with large-scale generation, purification and storage of properly folded protein, obtaining glycosylated native protein, generation of an anti-protein immune response, and inability of protein to cross the blood-brain barrier in diseases having significant central nervous system involvement.

Gene therapy using recombinant vectors containing nucleic acid sequences that encode a functional protein, or genetically modified human cells that express a functional protein, is also being used to treat protein deficiencies and other disorders that benefit from protein replacement. Although promising, this approach is also limited by technical difficulties such as the inability of vectors to infect or transduce dividing cells, low expression of the target gene, and regulation of expression once the gene is delivered.

A third, relatively recent approach to treating protein deficiencies involves the use of small molecule inhibitors to reduce the natural substrate of deficient enzyme proteins, thereby ameliorating the pathology. This "substrate deprivation" approach has been specifically described for a class of about 40 related enzyme disorders called lysosomal storage disorders or glycosphingolipid storage disorders. These heritable disorders are characterized by deficiencies in lysosomal enzymes that catalyze the breakdown of glycolipids in cells, resulting in an abnormal accumulation of lipids which disrupts cellular function. The small molecule inhibitors proposed for use as therapy are specific for inhibiting the enzymes involved in synthesis of glycolipids, reducing the amount of cellular glycolipid that needs to be broken down by the deficient enzyme. This approach is also limited in that glycolipids are necessary for biological function, and excess deprivation may cause adverse effects. Specifically, glycolipids are used by the brain to send signals from the gangliosides of neurons to another. If there are too few or too many glycolipids, the ability of the neuron to send signals is impeded.

A fourth approach, discussed below as specific chaperone strategy, rescues mutant proteins from degradation in the endoplasmic reticulum.

Protein Processing in the Endoplasmic Reticulum

Proteins are synthesized in the cytoplasm, and the newly synthesized proteins are secreted into the lumen of the endoplasmic reticulum (ER) in a largely unfolded state. In general, protein folding is governed by the principle of self assembly. Newly synthesized polypeptides fold into their native conformation based on their amino acid sequences (Anfinsen et al., Adv. Protein Chem. 1975; 29:205-300). In vivo, protein folding is complicated, because the combination of ambient temperature and high protein concentration stimulates the process of aggregation, in which amino acids normally buried in the hydrophobic core interact with their neighbors non-specifically. To avoid this problem, protein folding is usually facilitated by a special group of proteins called molecular chaperones which prevent nascent polypeptide chains from aggregating, and bind to unfolded protein such that the protein refolds in the native conformation (Hartl, Nature 1996; 381:571-580).

Molecular chaperones are present in virtually all types of cells and in most cellular compartments. Some are involved in the transport of proteins and permit cells to survive under stresses such as heat shock and glucose starvation (Gething et al., Nature 1992; 355:33-45; Caplan, Trends Cell. Biol. 1999; 9:262-268; Lin et al., Mol. Biol. Cell. 1993; 4:109-1119; Bergeron et al., Trends Biochem. Sci. 1994; 19:124-128). Among the molecular chaperones, Bip (immunoglobulin heavy-chain binding protein, Grp78) is the best characterized chaperone of the ER (Haas, Curr. Top. Microbiol. Immunol. 1991; 167:71-82). Like other molecular chaperones, Bip interacts with many secretory and membrane proteins within the ER throughout their maturation, although the interaction is normally weak and short-lived when the folding proceeds smoothly. Once the native protein conformation is achieved, the molecular chaperone no longer interacts with the protein. Bip binding to a protein that fails to fold, assemble or be properly glycosylated, becomes stable, and leads to degradation of the protein through the ER-associated degradation pathway. This process serves as a "quality control" system in the ER, ensuring that only those properly folded and assembled proteins are transported out of the ER for further maturation, and improperly folded proteins are retained for subsequent degradation (Hurtley et al., Annu. Rev. Cell. Biol. 1989; 5:277-307).

Certain DNA mutations result in amino acid substitutions that further impede, and in many cases preclude, proper folding of the mutant proteins. To correct these misfoldings, investigators have attempted to use various molecules. High concentrations of glycerol, dimethylsulfoxide (DMSO), trimethylamine N-oxide (TMAO), or deuterated water have been shown to suppress the degradation pathway and increase the intracellular trafficking of mutant protein in several diseases (Brown et al., Cell Stress Chaperones 1996; 1:117-125; Burrows et al., Proc. Natl. Acad. Sci. USA. 2000; 97:1796-801). These compounds are considered non-specific chemical chaperones to improve the general protein folding, although the mechanism of the function is still unknown. The high doses of this class of compounds required for efficacy makes them difficult or inappropriate to use clinically, although they are useful for the biochemical examination of folding defect of a protein intracellularly. These compounds also lack specificity.

Specific Chaperone Strategy

Previous patents and publications described a therapeutic strategy for rescuing endogenous enzyme proteins, specifically misfolded lysosomal enzymes, from degradation by the ER quality control machinery. This strategy employs small molecule reversible competitive inhibitors specific for a defective lysosomal enzyme associated with a particular lysosomal disorder. The strategy is as follows: since the mutant enzyme protein folds improperly in the ER (Ishii et al., Biochem. Biophys. Res. Comm. 1996; 220: 812-815), the enzyme protein is retarded in the normal transport pathway (ER→Golgi apparatus→endosome→lysosome) and rapidly degraded. Therefore, a functional compound which facilitates the correct folding of a mutant protein will serve as a site-specific chaperone for the mutant protein to promote the smooth escape from the ER quality control system. Since some inhibitors of an enzyme are known to occupy the catalytic center of enzyme, resulting in stabilization of its conformation in vitro. These specific chaperones may be designated active site-specific chaperones (ASSC).

The strategy has been specifically demonstrated for enzymes involved in the lysosomal storage disorders in U.S. Pat. Nos. 6,274,597, 6,583,158, 6,589,964, and 6,599,919, to Fan et al., and in pending U.S. application Ser. No. 10/304,396 filed Nov. 26, 2002, which are hereby incorporated herein by reference in their entirety. For example, a small molecule derivative of galactose, 1-deoxygalactonojirimycin (DGJ), a potent competitive inhibitor of the mutant Fabry enzyme α-galactosidase A (α-Gal A), effectively increased in vitro stability of a mutant α-Gal A (R301Q) at neutral pH and enhanced the mutant enzyme activity in lymphoblasts established from Fabry patients with R301Q or Q279E mutations. Furthermore, oral administration of DGJ to transgenic mice overexpressing a mutant (R301Q) α-Gal A substantially elevated the enzyme activity in major organs (Fan et al., Nature Med. 1999; 5: 112-115). Successful rescue of a misfolded protein depends on achieving a concentration of the specific inhibitor in vivo that is lower than necessary to completely inhibit the enzyme, in contrast to the substrate deprivation approach in which enzyme inhibitory concentrations are required.

In addition to the lysosomal storage disorders, a large and diverse number of diseases are now recognized as conformational diseases that are caused by adoption of non-native protein conformations, which may lead to retardation of the protein in the ER and ultimate degradation of the proteins (Kuznetsov et al., N. Engl. J. Med. 1998; 339:1688-1695; Thomas et al., Trends Biochem. Sci. 1995; 20:456-459; Bychkova et al., FEBS Lett. 1995; 359:6-8; Brooks, FEBS Lett. 1997; 409:115-120). ASSC's have been shown to rescue expression of mutant proteins other than enzymes. For example, small synthetic compounds were found to stabilize the DNA binding domain of mutant forms of the tumor suppressor protein p53, thereby allowing the protein to maintain an active conformation (Foster et al., Science 1999; 286:2507-10). Synthesis of receptors has been shown to be rescued by small molecule receptor antagonists and ligands (Morello et al., J. Clin. Invest. 2000; 105: 887-95; Petaja-Repo et al., EMBO J. 2002; 21:1628-37.) Even pharmacological rescue of membrane channel proteins and other plasma membrane transporters has been demonstrated using channel-blocking drugs or substrates (Rajamani et al., Circulation 2002; 105:2830-5; Zhou et al., J. Biol. Chem. 1999; 274:31123-26; Loo et al., J. Biol. Chem 1997; 272: 709-12). All of the above references indicate that ASSC's are capable of specific rescue of mutant proteins including, but not limited to, enzymes, receptors, membrane channel proteins, and DNA transcription factors.

In addition to mutant proteins, ASSC's have also been shown to stabilize wild-type proteins, resulting in their enhanced production and stability. As one example, it has been demonstrated that a specific ASSC, DGJ, is able to increase the amount and activity of wild-type α-Gal A in COS-7 cells transfected with a vector coding the wild-type α-Gal A sequence. The ASSC rescues the overexpressed wild-type enzyme, which is otherwise retarded in the ER quality control system, because overexpression and over production of the enzyme in the COS-7 cells exceeds the capacity of the system and leads to aggregation and degradation (see U.S. application Ser. No. 10/377,179, filed Feb. 28, 2003).

In summary, there is a need in the art for methods of improving the biological and cost efficiency of protein replacement therapy, such as for the treatment of protein deficiencies or other disorders whereby replacement proteins are administered.

SUMMARY OF THE INVENTION

The present invention provides a method for enhancing the stability of a purified protein, which method comprises contacting the protein in a pharmaceutically acceptable carrier with an active site-specific chaperone.

The purified protein can be a recombinant protein, and either full-length or truncated while retaining activity.

The present invention also provides a method of increasing in vitro the shelf-life of a protein by contacting the protein in a pharmaceutically acceptable carrier with an active site-specific chaperone.

The protein in the pharmaceutically acceptable carrier can be lyophilized or an aqueous solution.

The present invention further provides a method of extending the half-life and prolonging the activity in vivo of a purified protein in an individual who has been administered the protein in a pharmaceutically acceptable carrier, which method comprises contacting the protein with an active site-specific chaperone in a pharmaceutically acceptable carrier.

The present invention provides a method of treatment for an individual having a disorder requiring protein replacement, (e.g., protein deficiency disorders) comprising administering to the individual a purified replacement protein and an active site-specific chaperone (ASSC) capable of stabilizing the replacement protein.

In one embodiment, the replacement protein is a protein associated with a conformational disorder.

In a preferred embodiment, the conformational disorder is a lysosomal storage disorder.

In one embodiment, the lysosomal storage disorder is Fabry disease.

In another embodiment, the lysosomal storage disorder is Gaucher disease.

The invention also provides a method for enhancing the stability of a mutant, endogenous protein that is deficient due to defective folding or processing in the ER concurrently with protein replacement therapy. Stability and, hence, activity of the endogenous protein will be enhanced concurrently with the increased stability of the administered replacement protein that corresponds to the mutant protein.

The invention further provides a method for increasing the production of recombinant protein by non-mammalian host cells by contacting the host cell in a medium comprising an ASSC for the protein.

The invention further provides a composition comprising a purified protein and an ASSC for the purified protein in a pharmaceutically acceptable carrier.

BRIEF DESCRIPTION OF THE DRAWINGS

FIG. 1 demonstrates improved stability of both wild type α-Gal A purified from culture medium of Sf-9 cells infected with recombinant baculovirus carrying human wild type α-Gal A cDNA, and mutant α-Gal A collected as homogenates of hearts of transgenic mice overexpressing human mutant (R301Q) α-Gal A, respectively, using a site-specific chaperone 1-deoxygalactonojirimycin (DGJ, 1 μM). The mice were treated with 0.5 mM DGJ as drinking water for one week prior to the experiment. The mutant (A) and wild type (B) enzymes were pre-incubated with 0.1 M citrate-phosphate buffer (pH 7.0) at 37° C. for the mutant enzyme and 42° C. for the wild type enzyme, respectively, in the presence of DGJ at a concentration of 1 μM (○), 0.1 μM (●), 0.03 μM (◆) or 0 μM (no DGJ; ◇). Enzyme activity is reported relative to the enzyme without pre-incubation. DGJ can serve as a stabilizer to prevent the denaturation/degradation of the mutant and wild type enzymes.

DETAILED DESCRIPTION

The present invention advantageously improves the efficiency of protein replacement therapy to treat diseases or disorders by contacting the protein with an active site-specific chaperone (ASSC). The advantages of the invention flow from (a) increased efficiency of protein production from non-mammalian cells; (b) increased stability of the therapeutic protein, manifested by longer shelf life and better in vivo half life and activity; (c) maintenance of protein active site structure during translocations in vivo, including across cell membranes; and (d) rescue of endogenous mutant protein that is misfolded during synthesis and consequently cleared from the endoplasmic reticulum.

The present invention further provides formulations comprising the protein and active site-specific chaperone (ASSC) specific for the stabilization of the protein.

The invention is based on the discovery that ASSC's can be used as a combination therapy with protein replacement therapy for the treatment of genetic and other disorders. ASSC's can be screened and identified using methods known in the art. Once a specific ASSC useful for a particular disorder is identified, the ASSC can be administered to a patient receiving protein replacement therapy to enhance uptake of the replacement protein in the appropriate cellular compartment, improve stability of the protein in circulation and, if necessary, during transport into the cell. The chaperone can stabilize the protein in its active form during manufacture, storage and use in vivo.

DEFINITIONS

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

Specific Definitions.

The term "protein replacement" refers to the introduction of a non-native, purified protein into an individual having a deficiency in such protein. The administered protein can be obtained from natural sources (such as human gammaglobulin for treating RSV or mononucleosis) or by recombinant expression (as described in greater detail below). The term also refers to the introduction of a purified protein in an individual otherwise requiring or benefiting from administration of a purified protein, e.g., suffering from protein insufficiency. The introduced protein may be a purified, recombinant protein produced in vitro, or protein purified from isolated tissue or fluid, such as, e.g, placenta or animal milk, or from plants.

The term "disorder characterized by a protein deficiency" refers to any disorder that presents with a pathology caused by absent or insufficient amounts of a protein. This term encompasses protein folding disorders, i.e., conformational disorders, that result in a biologically inactive protein product. Protein insufficiency can be involved in infectious diseases, immunosuppression, organ failure, glandular problems, radiation illness, nutritional deficiency, poisoning, or other environmental or external insults.

The term "stabilize a proper conformation" refers to the ability of a compound or peptide or other molecule to associate with a wild-type protein, or to a mutant protein that can perform its wild-type function in vitro in, e.g., a formulation, and in vivo, in such a way that the structure of the wild-type or mutant protein can be maintained as its native or proper form. This effect may manifest itself practically through one or more of (i) increased shelf-life of the protein; (ii) higher activity per unit/amount of protein; or (iii) greater in vivo efficacy. It may be observed experimentally through increased yield from the ER during expression; greater resistance to unfolding due to temperature increases, or the present of chaotropic agents, and by similar means.

As used herein, the term "conformational disorder" or "conformational disease" refers to a disorder that is caused by adoption of a protein conformation that is not normally formed by a wild-type protein in a native condition with normal biological activity, which may lead to retardation and destruction of a protein in the ER. The decreased protein level results in a physiological imbalance that manifests itself as a disease or disorder. In a specific embodiment, the conformational disorder is a lysosomal storage disorder.

As used herein, the term "active site" refers to the region of a protein that has some specific biological activity. For example, it can be a site that binds a substrate or other binding partner and contributes the amino acid residues that directly participate in the making and breaking of chemical bonds. Active sites in this invention can encompass catalytic sites of enzymes, antigen biding sites of antibodies, ligand binding domains of receptors, binding domains of regulators, or receptor binding domains of secreted proteins. The active sites can also encompass transactivation, protein-protein interaction, or DNA binding domains of transcription factors and regulators.

As used herein, the term "active site-specific chaperone" refers to any molecule including a protein, peptide, nucleic acid, carbohydrate, etc. that specifically interacts reversibly with an active site of a protein and enhances formation of a stable molecular conformation. As used herein, "active site-specific chaperone" does not include_endogenous general chaperones present in the ER of cells such as Bip, calnexin or calreticulin, or general, non-specific chemical chaperones such as deuterated water, DMSO, or TMAO.

General Definitions.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 95% pure; more preferably, at least 97% pure, and more preferably still at least 99% pure. Purity can be evaluated by chromatography, gel electrophoresis, immunoassay, composition analysis, biological assay, and other methods known in the art. In a specific embodiment, purified means that the level of contaminants is below a level acceptable to regulatory authorities for administration to a human or non-human animal.

In preferred embodiments, the terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

A "gene" is a sequence of nucleotides which code for a functional "gene product". Generally, a gene product is a functional protein. However, a gene product can also be another type of molecule in a cell, such as an RNA (e.g., a tRNA or a rRNA). For the purposes of the present invention, a gene product also refers to an mRNA sequence which may be found in a cell.

The term "express" and "expression" means allowing or causing the information in a gene or DNA sequence to become manifest, for example producing RNA (such as rRNA or mRNA) or a protein by activating the cellular functions involved in transcription and translation of a corresponding gene or DNA sequence. A DNA sequence is expressed by a cell to form an "expression product" such as an RNA (e.g., a mRNA or a rRNA) or a protein. The expression product itself, e.g., the resulting RNA or protein, may also be said to be "expressed" by the cell.

The term "transfection" means the introduction of a foreign nucleic acid into a cell. The term "transformation" means the introduction of a "foreign" (i.e., extrinsic or extracellular) gene, DNA or RNA sequence into a host cell so that the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell or cells of a different genus or species.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence.

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells such as Sf9, Hi5 or S2 cells and Baculovirus vectors, and expression systems, and mammalian host cells and vectors.

The terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence.

As used herein the term "mutant protein" refers to proteins translated from genes containing genetic mutations that result in altered protein sequences. In a specific embodiment, such mutations result in the inability of the protein to achieve its native conformation under the conditions normally present in the ER. The failure to achieve this conformation results in these proteins being degraded, rather than being transported through their normal pathway in the protein transport system to their proper location within the cell. Other mutations can result in decreased activity or more rapid turnover.

A "wild-type gene" refers to a nucleic acid sequences which encodes a protein capable of having normal biological functional activity in vivo. The wild-type nucleic acid sequence may contain nucleotide changes that differ from the known, published sequence, as long as the changes result in amino acid substitutions having little or no effect on the biological activity. The term wild-type may also include nucleic acid sequences engineered to encode a protein capable of increased or enhanced activity relative to the endogenous or native protein.

A "wild-type protein" refers to any protein encoded by a wild-type gene that is capable of having functional biological activity when expressed or introduced in vivo. The term "normal wild-type activity" refers to the normal physiological function of a protein in a cell. Such functionality can be tested by any means known to establish functionality of a protein.

The term "genetically modified" refers to cells that express a particular gene product following introduction of a nucleic acid comprising a coding sequence which encodes the gene product, along with regulatory elements that control expression of the coding sequence. Introduction of the nucleic acid may be accomplished by any method known in the art including gene targeting and homologous recombination. As used herein, the term also includes cells that have been engineered to express or overexpress an endogenous gene or gene product not normally expressed by such cell, e.g., by gene activation technology.

The phrase "pharmaceutically acceptable", whether used in connection with the pharmaceutical compositions of the invention, refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The terms "therapeutically effective dose" and "effective amount" refer to the amount of the compound that is sufficient to result in a therapeutic response. In embodiments where an ASSC and protein are administered in a complex, the terms "therapeutically effective dose" and "effective amount" may refer to the amount of the complex that is sufficient to result in a therapeutic response. A therapeutic response may be any response that a user (e.g., a clinician) will recognize as an effective response to the therapy. Thus, a therapeutic response will generally be an amelioration of one or more symptoms of a disease or disorder.

It should be noted that a concentration of the ASSC that is inhibitory during in vitro production, transportation, or storage of the purified therapeutic protein may still constitute an "effective amount" for purposes of this invention because of dilution (and consequent shift in binding due to the change in equilibrium), bioavailability and metabolism of the ASSC upon administration in vivo.

Disorders Characterized by Protein Deficiencies

There currently are about 1100 known inherited disorders characterized by protein deficiency or loss-of-function in specific tissue. These disorders may be treatable by protein replacement therapy in theory. The method of the present invention contemplates co-therapy for proteins currently suited for use in protein replacement therapy that is available now or will be in the future. In such disorders, certain cells or all of the cells of an individual lack a sufficient functional protein, contain an inactive form of the protein or contain insufficient levels for biological function.

Further, the list of diseases identified as being conformational disorders, caused by mutations that alter protein folding and retardation of the mutant protein in the ER, resulting in protein deficiency, is increasing. These include cystic fibrosis, α1-antitrypsin deficiency, familial hypercholesterolemia, Fabry disease, Alzheimer's disease (Selkoe, Annu. Rev. Neurosci. 1994; 17:489-517), osteogenesis imperfecta (Chessler et al., J. Biol. Chem. 1993; 268:18226-18233), carbohydrate-deficient glycoprotein syndrome (Marquardt et al., Eur. J. Cell. Biol. 1995; 66: 268-273), Maroteaux-Lamy syndrome (Bradford et al., Biochem. J. 1999; 341:193-201), hereditary blindness (Kaushal et al., Biochemistry 1994; 33:6121-8), Glanzmann thrombasthenia (Kato et al., Blood 1992; 79:3212-8), hereditary factor VII deficiency (Arbini et al., Blood 1996; 87:5085-94), oculocutaneous albinism (Halaban et al., Proc. Natl. Acad. Sci. USA. 2000; 97:5889-94) and protein C deficiency (Katsumi, et al., Blood 1996; 87:4164-75). Recently, one mutation in the X-linked disease adrenoleukodystrophy (ALD), resulted in misfolding of the defective peroxisome transporter which could be rescued by low-temperature cultivation of affected cells (Walter et al., Am J Hum Genet 2001; 69:35-48). It is generally accepted that mutations take place evenly over the entire sequence of a gene. Therefore, it is predictable that the phenotype resulting from misfolding of the deficient protein exists in many other genetic disorders.

Lysosomal Storage Disorders

Many of the inherited protein deficient disorders are enzyme deficiencies. As indicated above, a large class of inherited enzyme disorders involves mutations in lysosomal enzymes and are referred to as lysosomal storage disorders (LSDs). Lysosomal storage disorders are a group of diseases caused by the accumulation of glycosphingolipids, glycogen, mucopolysaccharides Examples of lysosomal disorders include but are not limited to Gaucher disease (Beutler et al., *The Metabolic and Molecular Bases of Inherited Disease*, 8*th ed.* 2001 Scriver et al., ed. pp. 3635-3668, McGraw-Hill, New York), GM1-gangliosidosis (id. at pp 3775-3810), fucosidosis (*The Metabolic and Molecular Bases of Inherited Disease* 1995. Scriver, C. R., Beaudet, A. L., Sly, W. S. and Valle, D., ed pp. 2529-2561, McGraw-Hill, New York), mucopolysaccharidoses (id. at pp 3421-3452), Pompe disease (id. at pp. 3389-3420), Hurler-Scheie disease (Weismann et al., Science 1970; 169, 72-74), Niemann-Pick A and B diseases, (*The Metabolic and Molecular Bases of Inherited Disease* 8*th ed.* 2001. Scriver et al. ed., pp 3589-3610, McGraw-Hill, New York), and Fabry disease (id. at pp. 3733-3774). A list of LSDs and their associated deficient enzymes can be found in Table 1 infra. Two are discussed specifically below.

Fabry Disease

Fabry disease is an X-linked inborn error of glycosphingolipid metabolism caused by deficient lysosomal α-galactosidase A (α-Gal A) activity (Desnick et al., *The Metabolic and Molecular Bases of Inherited Disease*, 8$^{th}$ *Edition* Scriver et al. ed., pp. 3733-3774, McGraw-Hill, New York 2001; Brady et al., N. Engl. J. Med. 1967; 276, 1163-1167). This enzymatic defect leads to the progressive deposition of neutral glycosphingolipids with α-galactosyl residues, predominantly globotriaosylceramide (GL-3), in body fluids and tissue lysosomes. The frequency of the disease is estimated to be about 1:40,000 in males, and is reported throughout the world within different ethnic groups. In classically affected males, the clinical manifestations include angiokeratoma, acroparesthesias, hypohidrosis, and characteristic corneal and lenticular opacities (*The Metabolic and Molecular Bases of Inherited Disease*, 8$^{th}$ *Edition* 2001, Scriver et al., ed., pp. 3733-3774, McGraw-Hill, New York). The affected male's life expectancy is reduced, and death usually occurs in the fourth or fifth decade as a result of vascular disease of the heart, brain, and/or kidneys. In contrast, patients with the milder "cardiac variant" normally have 5-15% of normal α-Gal A activity, and present with left ventricular hypertrophy or a cardiomyopathy. These cardiac variant patients remain essentially asymptomatic when their classically affected counterparts are severely compromised. Recently, cardiac variants were found in 11% of adult male patients with unexplained left ventricular hypertrophic cardiomyopathy, suggesting that Fabry disease may be more frequent than previously estimated (Nakao et al., N. Engl. J. Med. 1995; 333: 288-293). The α-Gal A gene has been mapped to Xq22, (Bishop et al., Am. J. Hum. Genet. 1985; 37: A144), and the full-length cDNA and entire 12-kb genomic sequences encoding αGal A have been reported (Calhoun et al., Proc. Natl. Acad. Sci. USA 1985; 82: 7364-7368; Bishop et al., Proc. Natl. Acad. Sci. USA 1986; 83: 4859-4863; Tsuji et al., Eur. J. Biochem. 1987; 165: 275-280; and Kornreich et al., Nucleic Acids Res. 1989; 17: 3301-3302). There is a marked genetic heterogeneity of mutations that cause Fabry disease (*The Metabolic and Molecular Bases of Inherited Disease, 8th Edition* 2001, Scriver et al., ed., pp. 3733-3774, McGraw-Hill, New York.; Eng et al., Am. J. Hum. Genet. 1993; 53: 1186-1197; Eng et al., Mol. Med. 1997; 3: 174-182; and Davies et al., Eur. J. Hum. Genet. 1996; 4: 219-224). To date, a variety of missense, nonsense, and splicing mutations, in addition to small deletions and insertions, and larger gene rearrangements have been reported.

Gaucher Disease

Gaucher disease is a deficiency of the lysosomal enzyme β-glucocerebrosidase that breaks down fatty glucocerebrosides. The fat then accumulates, mostly in the liver, spleen and bone marrow. Gaucher disease can result in pain, fatigue, jaundice, bone damage, anemia and even death. There are three clinical phenotypes of Gaucher disease. Patients with, Type 1 manifest either early in life or in young adulthood, bruise easily and experience fatigue due to anemia, low blood platelets, enlargement of the liver and spleen, weakening of the skeleton, and in some instances have lung and kidney impairment. There are no signs of brain involvement. In Type II, early-onset, liver and spleen enlargement occurs by 3 months of age and there is extensive brain involvement. There is a high mortality rate by age 2. Type III is characterized by liver and spleen enlargement and brain seizures. The β-glucocerebrosidase gene is located on the human 1q21 chromosome. Its protein precursor contains 536 amino acids and its mature protein is 497 amino acids long.

Gaucher disease is considerably more common in the descendants of Jewish people from Eastern Europe (Ashkenazi), although individuals from any ethnic group may be affected. Among the Ashkenazi Jewish population, Gaucher disease is the most common genetic disorder, with an incidence of approximately 1 in 450 persons. In the general public, Gaucher disease affects approximately 1 in 100,000 persons. According to the National Gaucher Foundation, 2,500 Americans suffer from Gaucher disease.

Other Enzyme Deficiency Disorders

Glucose-6-phosphate dehydrogenase (G6PD) deficiency is the most common X-linked human enzyme deficiency. The G6PD enzyme catalyzes an oxidation/reduction reaction that is essential for the production of ribose, which is an essential component of both DNA and RNA. G6PD also involved in maintaining adequate levels of NADPH inside the cell. NADPH is a required cofactor in many biosynthetic reactions. Individuals with this deficiency have clinical symptoms including neonatal jaundice, abdominal and/or back pain, dizziness, headache, dyspnea (irregular breathing), and palpitations.

In addition to inherited disorders, other enzyme deficiencies arise from damage to a tissue or organ resulting from primary or secondary disorders. For example, damaged pancreatic tissue, or pancreatitis, is caused by alcoholism results in a deficiency in pancreatic enzymes necessary for digestion. Pancreatitis is currently being treated using enzyme replacement therapy.

TABLE 1

Lysosomal Storage Disorders, Associated Defective Enzymes and Small Molecule Active Site-Specific Chaperones

| DISORDER | DEFICIENT ENZYME | REVERSIBLE CHAPERONE |
| --- | --- | --- |
| Pompe disease | α-Glucosidase | 1-deoxynojirimycin (DNJ) |
| | | α-homonojirimycin |
| | | castanospermine |
| Gaucher disease | Acid β-Glucosidase (glucocerebrosidase) | isofagomine |
| | | N-dodecyl-DNJ |
| | | calystegines $A_3$, $B_1$, $B_2$ and $C_1$ |
| Fabry disease | α-Galactosidase A | 1-deoxygalactonojirimycin (DGJ) |
| | | α-allo-homonojirimycin |
| | | α-galacto-homonojirimycin |
| | | β-1-C-butyl-deoxynojirimycin |
| | | calystegines $A_2$ and $B_2$ |
| | | N-methyl calystegines $A_2$ and $B_2$ |
| $G_{M1}$-gangliosidosis | Acid β-Galactosidase | 4-epi-isofagomine |
| | | 1-deoxygalactonojirimycin |
| Krabbe disease | Galactocerebrosidase | 4-epi-isofagomine |
| | | 1-deoxygalactonojirimycin |
| Morquio disease B | Acid β-Galactosidase | 4-epi-isofagomine |
| | | 1-deoxygalactonojirimycin |
| α-Mannosidosis | Acid α-Mannosidase | 1-deoxymannojirimycin |
| | | Swainsonine |
| | | Mannostatin A |
| β-Mannosidosis | Acid β-Mannosidase | 2-hydroxy-isofagomine |
| Fucosidosis | Acid α-L-fucosidase | 1-deoxyfuconojirimycin |
| | | β-homofuconojirimycin |
| | | 2,5-imino-1,2,5-trideoxy-L-glucitol |
| | | 2,5-deoxy-2,5-imino-D-fucitol |
| | | 2,5-imino-1,2,5-trideoxy-D-altritol |

TABLE 1-continued

Lysosomal Storage Disorders, Associated Defective Enzymes and Small Molecule Active Site-Specific Chaperones

| DISORDER | DEFICIENT ENZYME | REVERSIBLE CHAPERONE |
|---|---|---|
| Sanfilippo disease B | α-N-Acetylglucosaminidase | 1,2-dideoxy-2-N-acetamido-nojirimycin |
| Schindler disease | α-N-Acetylgalactosaminidase | 1,2-dideoxy-2-N-acetamido-galactonojirimycin |
| Tay-Sachs disease | β-Hexosaminidase A | 2-N-acetylamino-isofagomine<br>1,2-dideoxy-2-acetamido-nojirimycin<br>nagstain |
| Sandhoff disease | β-Hexosaminidase B | 2-N-acetamido-isofagomine<br>1,2-dideoxy-2-acetamido-nojirimycin<br>nagstain |
| Hurler-Scheie disease | α-L-Iduronidase | 1-deoxyiduronojirimycin<br>2-carboxy-3,4,5-trideoxypiperidine |
| Sly disease | β-Glucuronidase | 6-carboxy-isofagomine<br>2-carboxy-3,4,5-trideoxypiperidine |
| Sialidosis | Sialidase | 2,6-dideoxy-2,6,imino-sialic acid<br>Siastatin B |
| Hunter disease | Iduronate sulfatase | 2,5-anhydromannitol-6-sulphate |
| Niemann-Pick disease | Acid sphingomyelinase | desipramine, phosphatidylinositol-4,5-diphosphate |

Other Disorders Treated Using Protein Replacement

In addition to disorders characterized by protein deficiencies, some disorders are treated by administration of replacement proteins to enhance or stimulate biological processes. For example, individuals with anemia are administered recombinant erythropoietin (EPOGEN®, PROCRIT®, EPOIETIN®) to stimulate red blood cell production and increase oxygen transportation to tissues. In addition, recombinant interferons such as interferon alpha 2b (INTRON A®, PEG-INTRON®, or REBETOL®), and interferon beta 1a (AVONEX®, BETASERON®) are administered to treat hepatitis B and multiple sclerosis, respectively. Still other proteins administered are recombinant human deoxyribonuclease I (rhDNase-PULMOZYME®), an enzyme which selectively cleaves DNA used to improve pulmonary function in patients with cystic fibrosis; recombinant thyroid stimulating hormone (THYROGEN®) developed for use in thyroid cancer patients who have had near-total or total thyroidectomy, and who must therefore take thyroid hormones; recombinant G-CSF (NEUPOGEN®) for treating neutropenia from chemotherapy, and digestive enzymes in individuals with pancreatitis. Another significant area of protein therapy is in the treatment of infectious diseases and cancer with antibodies, which have a highly specific, well-defined active site. Antibody therapeutic products include RESPIRGRAM® for respiratory syncitial virus, HERCEPTIN®, for breast cancer; REMICAID® and HUMIRA®, for arthritis and inflammatory diseases, and others. ASSCs for antibodies are well known, and either the target antigen or a structurally related analog (e.g., a modified form of the active target or a mimetic) can be employed. See Table 2 below for a list of proteins currently on the market or being evaluated in clinical trials for use as protein therapy.

TABLE 2

Replacement Proteins Administered in Associated Disorders

| Protein | Trade name | Therapeutic function | Development phase |
|---|---|---|---|
| (rhuMAb-VEGF) | Dynepo ™ | anemia associated with renal disease | Phase III |
| α-L-iduronidase | Aldurazyme ™ | mucopolysaccharidosis-I | Commercially available |
| alronidase | rDNA insulin | diabetes | Phase III |
| alteplase, | Activase ® | acute myocardial infarction; acute massive pulmonary embolism; ischemic stroke within 3 to 5 hours of symptom onset | Commercially available |
| darbepoetin alfa | Aranesp ™ | anemia | Commercially available |
| Deoxyribonuclease I | Pulmozyme | cystic fibrosis | Commercially available |
| drotrecogin alfa (activated protein C) | Xigris ™ | severe sepsis | Commercially available |
| efalizumab | Raptiva ® | moderate to severe psoriasis | Commercially available |
| erythropoietin | EPOGEN ® | anemia | Commercially available |

TABLE 2-continued

Replacement Proteins Administered in Associated Disorders

| Protein | Trade name | Therapeutic function | Development phase |
|---|---|---|---|
| erythropoietin | PROCRIT ® | anemia | Commercially available |
| etanercept | Enbrel ® | rheumatoid arthritis; psoriatic arthritis | Commercially available |
| factor IX | BeneFIX ™ | hemophilia B | Commercially available |
| follicle-stimulating hormone | Follistim ® | infertility | Commercially available |
| G-CSF | Neupogen | neutropenia resulted from Chemotherapy | Commercially available |
| glucocerebrosidase | Cerezyme ™ | Gaucher's disease | Commercially available |
| GM-CSF | KGF (Repifermin) | mucositis | Phase III completed |
| Growth hormone | BioTropin ™ | growth hormone deficiency in children | Commercially available |
| heat shock protein | Leukine ® | mucositis and melanoma | Commercially available |
| Insulin | Humalog ® | diabetes | Commercially available |
| interferon | Actimmune ® | idiopathic pulmonary fibrosis | Commercially available |
| interferon alfa | Enbrel ® (enterecept) | ankylosing spondylitis, psoriasis | Commercially available |
| interferon alfa-2a, | Roferon ®-A | hairy cell leukemia; Kaposi's sarcoma; chronic recombinant myelogenous leukemia; hepatitis C | Commercially available |
| interferon alfa-n3 | Actimmune ® | systemic fungal infections | Commercially available |
| interferon alfa-n3 | Alferon N | genital warts | Commercially available |
| interferon beta-1a | Avonex ® | relapsing multiple sclerosis | Commercially available |
| interferon beta-1a | Pegasys ® | chronic hepatitis C | Commercially available |
| interferon beta-1b | Betaseron ® | relapsing, remitting multiple sclerosis | Commercially available |
| interferon beta-1b | Rebif ® | chronic hepatitis C | Commercially available |
| interferon gamma 1b | Actimmune ® | chronic granulomatous disease; osteopetrosis | Commercially available |
| agalsidase beta | Fabrazyme ™ | Fabry disease | Commercially available |
| interleukin-2 | Proleukin ® | renal cell carcinoma; metastatic melanoma | Commercially available |
| keratinocyte growth factor | Avastin ™ | colorectal cancer | Phase III completed |
| lepirudin (anticoagulant) | Refludan ™ | heparin-induced. thrombocytopenia type II | Commercially available |
| omalizumab | Xolair ® | allergy-related asthma | Commercially available |
| rasburicase | Elitek ® | hyperuricemia, | Commercially available |
| reteplase (tissue plasminogen factor) | Retavase ® | acute myocardial infarction | Commercially available |
| thyroid stimulating hormone | Thyrogen ® | thyroid cancer | Commercially available |
| TNF-alpha | Oncophage ® | colorectal, renal cell cancer, melanoma | Phase III |
| trastuzumab | Herceptin ® | HER2 overexpressing metastatic breast cancer | Commercially available |

Treatment of Protein Deficiencies and Other Disorders

As mentioned briefly above, gene therapy, protein replacement therapy, and small molecule inhibitor therapy have been developed as therapeutic strategies for the treatment of genetic disorders resulting from protein deficiencies and for disorders that benefit from administration of replacement proteins.

Protein replacement therapy increases the amount of protein by exogenously introducing wild-type or biologically functional protein by way of infusion. This therapy has been developed for many genetic disorders including Gaucher disease and Fabry disease, as referenced above. The wild-type enzyme is purified from a recombinant cellular expression system (e.g., mammalian cells or insect cells-see U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al.; and U.S. Pat. No. 5,879,680 to Ginns et al.), human placenta, or animal milk (see U.S. Pat. No. 6,188,045 to Reuser et al.). After the infusion, the exogenous enzyme is expected to be taken up by tissues through non-specific or receptor-specific mechanism. In general, the uptake efficiency is not high, and the circulation time of the exogenous protein is short (Ioannu et al., Am. J. Hum. Genet. 2001; 68: 14-25). In addition, the exogenous protein is unstable and subject to rapid intracellular degradation.

In addition to protein replacement and gene therapy, small molecule therapy using enzyme inhibitors has been described for the treatment of the LSD's, namely small molecule inhibitors useful for substrate deprivation of the precursors of the deficient enzyme, referenced above. Small molecule inhibitors have been described for the treatment of LSD's including Fabry disease, Gaucher disease, Pompe disease, Tay Sachs disease, Sandhoff disease, and $G_{M2}$ gangliosidoses (see U.S. Pat. Nos. 5,472,969, 5,580,884, 5,798,366, and 5,801,185 to Platt et al.).

Co-Therapy Using ASSC's and Protein Replacement

The present invention increases the effectiveness of protein replacement therapy by increasing the stability of the purified protein in vitro in a formulation or composition, and in vivo by co-administration of an ASSC for the protein. Screening for an appropriate ASSC for the target protein can be achieved using ordinary methods in the art, for example, as described in U.S. patent application Ser. No. 10/377,179, filed Feb. 28, 2003, which is incorporated herein by reference.

Replacement Protein Production

Disorders that can be treated using the method of the present invention include but are not limited to LSD's, glucose-6-phosophate dehydrogenase deficiency, hereditary emphysema, familial hypercholesterolemia, familial hypertrophic cardiomyopathy, phenylketonuria, anemia, hepatitis B and multiple sclerosis.

The replacement proteins useful for the methods of the present invention can be isolated and purified using ordinary molecular biology, microbiology, and recombinant DNA techniques within the skill of the art. For example, nucleic acids encoding the replacement protein can be isolated using recombinant DNA expression as described in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. ÊHiggins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. ÊPerbal, *A Practical Guide To Molecular Cloning* (1984); F. M. Ausubel et al. (eds.), *Current Protocols in Molecular Biology*, John Wiley & Sons, Inc. (1994). The nucleic acid encoding the protein may be full-length or truncated, as long as the gene encodes a biologically active protein. For example, a biologically active, truncated form of α-Gal A, the defective enzyme associated with Fabry disease, has been described in U.S. Pat. No. 6,210,666 to Miyamura et al.

The identified and isolated gene encoding the target protein can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Production of the recombinant protein can be maximized by genetic manipulations such as including a signal peptide at the N terminus to facilitate secretion or a 3' untranslated sequence containing a polyadenylation site.

In a preferred embodiment, the constructs used to transduce host cells are viral-derived vectors, including but not limited to adenoviruses, adeno-associated viruses, herpes virus, mumps virus, poliovirus, retroviruses, Sindbis virus and vaccinia viruses.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed, such as glycosylation, sialyation and phosphorylation. For example, expression in a bacterial system can be used to produce an nonglycosylated core protein product. However, protein expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, protein. Furthermore, different vector/host expression systems may affect processing reactions, such as proteolytic cleavages, to a different extent. The expression efficiency can be increased by use of a specific chaperone, as described in U.S. Pat. No. 6,274,597, and related family members disclosed above.

Purification of recombinantly expressed protein can be achieved using methods known in the art such as by ammonium sulfate precipitation, column chromatography containing hydrophobic interaction resins, cation exchange resins, anion exchange resins, and chromatofocusing resins. Alternatively, imunoaffinity chromatography can be used to purify the recombinant protein using an appropriate polyclonal or monoclonal antibody that binds specifically to the protein, or to a tag that is fused to the recombinant protein. In a preferred embodiment, the purity of the recombinant protein used for the method of the present invention with be at least 95%, preferably 97% and most preferably, greater than 98%.

Replacement Protein Administration

Numerous methods can be employed to achieve uptake and targeting of the replacement protein by the cells. Peptide sequences have been identified that mediate membrane transport, and accordingly provide for delivery of polypeptides to the cytoplasm. For example, such peptides can be derived from the Antennapedia homeodomain helix 3 to generate membrane transport vectors, such as penetratin (PCT Publication WO 00/29427; see also Fischer et al., J. Pept. Res. 2000; 55:163-72; DeRossi et al., Trends in Cell Biol. 1998; 8:84-7; Brugidou et al., Biochem. Biophys. Res. Comm. 1995; 214:685-93), the VP22 protein from herpes simplex virus (Phelan et al., Nat. Biotechnol. 1998; 16:440-3), and the HIV TAT trascriptional activator. Protein transduction domains, including the Antennapedia domain and the HIV TAT domain (see Vives et al., J. Biol. Chem. 1997; 272:16010-17), possess a characteristic positive charge, which led to the development of cationic 12-mer peptides that can be used to transfer therapeutic proteins and DNA into cells (Mi et al., Mol. Therapy 2000; 2:339-47). The above-mentioned protein transduction domains are covalently linked to the target protein, either by chemical covalent cross-linking or generation as a fusion protein. Further, a non-covalent, synthetic protein transduction domain has been recently developed by Active Motif Inc. (Carlsbad, Calif.). This domain associates with the target protein through hydrophobic interactions, and advantageously dissociates from the protein once inside the cell (Morris et al., Nat. Biotechnol. 2001; 19:1173-6). In addition, lipid carriers have recently been shown to deliver proteins into cells in addition to an established use for delivering naked DNA (Zelphati et al., J. Biol. Chem. 2001; 276:35103-10). For an overview of protein translocation techniques see Bonetta, The Scientist 2002; 16(7):38.

In specific embodiments, the replacement proteins used in the method of the present invention are enzymes associated with lysosomal storage disorders (see Table 1). Sequences of nucleic acids encoding wild-type versions of such enzymes can be found in the literature or in public databases such as GenBank, e.g., X14448 for α-Gal A (AGA), J03059 for human glucocerebrosidase (GCB), M74715 for human α-L-iduronidase (IDUA), M34424 for human acid α-glucosidase (GAA), AF011889 for human iduronate 2-sulfatase (IDS), and M59916 for human acid sphingomyelinase (ASM).

Enzyme replacement in LSDs.

Several replacement enzymes for LSDs are currently available in Europe and the U.S. These include Cerezyme®, recombinant form of glucerebrosidase for the treatment of Gaucher disease; Fabrazyme®, recombinant form of alpha galactosidase A; Aldurazyme™, a recombinant enzyme for the treatment of MPS1, all from Genzyme Corp. and recombinant alpha glucosidase for patients with Pompe disease (Van den Hout et al., Lancet 2000; 56:397-8).

Active Site-Specific Chaperones

ASSC's contemplated by the present invention include but are not limited to small molecules (e.g., organic or inorganic molecules which are less than about 2 kD in molecular weight, are more preferably less than about 1 kD in molecular weight), including substrate or binding partner mimetics; small ligand-derived peptides or mimetics thereof; nucleic acids such as DNA, RNA; antibodies, including Fv and single chain antibodies, and Fab fragments; macromolecules (e.g., molecules greater than about 2 kD in molecular weight) and members of libraries derived by combinatorial chemistry, such as molecular libraries of D- and/or L-configuration amino acids; phosphopeptides, such as members of random or partially degenerate, directed phosphopeptide libraries (see, e.g., Songyang et al., Cell 1993; 72:767-778).

Synthetic libraries (Needels et al., Proc. Natl. Acad. Sci. USA 1993; 90:10700-4; Ohlmeyer et al., Proc. Natl. Acad. Sci. USA 1993; 90:10922-10926; Lam et al., PCT Publication No. WO 92/00252; Kocis et al., PCT Publication No. WO 94/28028) provide a source of potential ASSC's according to the present invention. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through Res. 1986; 155:119-29.

In a preferred embodiment, ASSC's useful for the present invention are inhibitors of lysosomal enzymes and include glucose and galactose imino-sugar derivatives as described in Asano et al., J. Med. Chem 1994; 37:3701-06; Dale et al., Biochemistry 1985; 24:3530-39; Goldman et al., J. Nat. Prod. 1996; 59:1137-42; Legler et al, Carbohydrate Res. 1986; 155:119-29. Such derivatives include but are not limited those compound listed in Table 1. Some of these compounds can be purchased from commercial sources such as Toronto Research Chemicals, Inc. (North York, On. Canada) and Sigma.

In a preferred embodiment, ASSC's useful for the present invention are activators of cystic fibrosis transmembrane conductance regulator (CFTR) which include benzo(c)quinolizinium compounds as described in Dormer et al., J. Cell Sci. 2001; 114: 4073-81; and Ma et al., J. Biol. Chem. 2002; 277: 37235-41.

In another preferred embodiment, ASSC's useful for the present invention are ligands of G protein-coupled receptors, such as ☐ opioid receptor, V2 vasopressin receptor, and photopigment rhodopsin, as described in Petaja-Repo et al., EMBO J 2002; 21: 1628-37; Morello et al., J. Clin. Invest. 2000; 105: 887-95; Saliba et al., J. Cell Sci. 2002; 115: 2907-18.

In another preferred embodiment, ASSC's useful for the present invention are compounds that stabilize the DNA binding domain of p53, as described in Foster et al., Science 1999; 286: 2507-10; Friedler et al., PNAS 2002; 99: 937-42.

In yet another preferred embodiment, ASSC's useful for the present invention are blockers of ion channel proteins, such as HERG potassium channel in human Long QT syndrome, pancereatic ATP-sensitive potassium ($K_{ATP}$)

Formulations

In one embodiment, the ASSC and replacement protein are formulated in a single composition. Such a composition enhances stability of the protein during storage and in vivo administration, thereby increasing therapeutic efficacy. The formulation is preferably suitable for parenteral administration, including intravenous subcutaneous, and intraperitoneal, however, formulations suitable for other routes of administration such as oral, intranasal, or transdermal are also contemplated.

In another embodiment, the replacement protein and the ASSC's are formulated in separate compositions. In this embodiment, the chaperone and the replacement protein may be administered according to the same route, e.g., intravenous infusion, or different routes, e.g., intravenous infusion for the replacement protein, and oral administration for the ASSC. The pharmaceutical formulations suitable for injectable use include sterile aqueous solutions (where water soluble) or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, benzyl alchohol, sorbic acid, and the like. In many cases, it will be preferable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the purified protein and ASSC in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Preferably the formulation contains an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The formulation also preferably contains a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

For lyophilization of protein and chaperone preparations, the protein concentration can be 0.1-10 mg/mL. Bulking agents, such as glycine, mannitol, albumin, and dextran, can be added to the lyophilization mixture. In addition, possible cryoprotectants, such as disaccharides, amino acids, and PEG, can be added to the lyophilization mixture. Any of the buffers, excipients, and detergents listed above, can also be added.

Formulations for inhalation administration may contain lactose or other excipients, or may be aqueous solutions which may contain polyoxyethylene-9-lauryl ether, glycocholate or deoxycocholate. A preferred inhalation aerosol is characterized by having particles of small mass density and large size. Particles with mass densities less than 0.4 gram per cubic centimeter and mean diameters exceeding 5 µm efficiently deliver inhaled therapeutics into the systemic circulation. Such particles are inspired deep into the lungs and escape the lungs' natural clearance mechanisms until the inhaled particles deliver their therapeutic payload. (Edwards et al., Science 1997; 276: 1868-1872). Replacement protein preparations of the present invention can be administered in aerosolized form, for example by using methods of preparation and formulations as described in, U.S. Pat. Nos. 5,654,007, 5,780,014, and 5,814,607, each incorporated herein by reference. Formulation for intranasal administration may include oily solutions for administration in the form of nasal drops, or as a gel to be applied intranasally.

Formulations for topical administration to the skin surface may be prepared by dispersing the composition with a dermatological acceptable carrier such as a lotion, cream, ointment, or soap. Particularly useful are carriers capable of forming a film or layer over the skin to localize application and inhibit removal. For topical administration to internal tissue surfaces, the composition may be dispersed in a liquid tissue adhesive or other substance known to enhance adsorption to a tissue surface. Alternatively, tissue-coating solutions, such as pectin-containing formulations may be used.

In preferred embodiments, the formulations of the invention are supplied in either liquid or powdered formulations in devices which conveniently administer a predetermined dose of the preparation; examples of such devices include a needle-less injector for either subcutaneous or intramuscular injection, and a metered aerosol delivery device. In other instances, the preparation may be supplied in a form suitable for sustained release, such as in a patch or dressing to be applied to the skin for transdermal administration, or via erodable devices for transmucosal administration. In instances where the formulation, e.g., the ASSC is orally administered in tablet or capsule form, the preparation might be supplied in a bottle with a removable cover or as blister patches.

In Vitro Stability.

Ensuring the stability of a pharmaceutical formulation during its shelf life is a major challenge. Prior to development of a protein pharmaceutical, inherent or latent instabilities within the active ingredients must be explored and addressed. Instability of protein and peptide therapeutics is classified as chemical instability or physical instability. Examples of chemical instability are hydrolysis, oxidation and deamidation. Examples of physical instability are aggregation, precipitation and adsorption to surfaces. In addition, a protein may be subjected to stresses such as pH, temperature, shear stress, freeze/thaw stress and combinations of these stresses.

One of the most prevalent formulation problems is product aggregation, resulting in a loss in bioactivity. The addition of excipients may slow the process but may not completely prevent it. Activity losses may or may not be detected by physical assays and are only evident in bioassays or potency assays with large (sometimes 15-20%) coefficients of variation, making it difficult to determine actual losses.

ASSC have been shown to enhance enzyme activity by preventing degradation of enzymes and aggregation of enzyme proteins (Fan et al., Nat. Med. 1999; 5: 112-5; FIG. 1). In the embodiment where the ASSC and the replacement protein are in the same composition, the formulated compositions of the invention may be provided in containers suitable for maintaining sterility, and importantly, protecting the activity of the replacement protein during proper distribution and storage. In addition to stabilizing the administered protein in vivo, the ASSC reversibly binds to and stabilizes the conformation of the replacement protein in vitro, thereby preventing aggregation and degradation, and extending the shelf-life of the formulation. Analysis of the ASSC/replacement protein interaction may be evaluated using techniques well-known in the art, such as, for example, differential scanning calorimetry, or circular dichroism.

For example, where an aqueous injectable formulation of the composition is supplied in a stoppered vial suitable for withdrawal of the contents using a needle and syringe, the presence of an ASSC inhibits aggregation of the replacement protein. The vial could be for either single use or multiple uses. The formulation can also be supplied as a prefilled syringe. In another embodiment, the formulation is in a dry or lyophilized state, which would require reconstitution with a standard or a supplied, physiological diluent to a liquid state. In this instance, the presence of an ASSC would stabilize the replacement protein during and post-reconstitution to prevent aggregation. In the embodiment where the formulation is a liquid for intravenous administration, such as in a sterile bag for connection to an intravenous administration line or catheter, the presence of an ASSC would confer the same benefit.

In addition to stabilizing the replacement protein to be administered, the presence of an ASSC may enable the pharmaceutical formulation to be stored at a neutral pH of about 7.0-7.5. This will confer a benefit to proteins that normally must be stored at a lower pH to preserve stability. For example, lysosomal enzymes, such as those listed in Table 1, retain a stable conformation at a low pH (e.g., 5.0 or lower). However, extended storage of the replacement enzyme at a low pH may expedite degradation of the enzyme and/or formulation.

Separate Formulations.

Where the replacement enzyme and ASSC are in separate formulations, the ASSC can be in a form suitable for any route of administration, including all of the forms described above, e.g., as sterile aqueous solution or in a dry lyophilized powder to be added to the formulation of the replacement protein during or immediately after reconstitution to prevent aggregation in vitro prior to administration. Alternatively, the ASSC can be formulated for oral administration in the form of tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

Administration

The route of administration may be oral or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations may be by periodic injections of a bolus of the preparation, or may be administered by intravenous or intraperitoneal administration from a reservoir which is external (e.g., an i.v. bag) or internal (e.g., a bioerodable implant, a bioartificial organ, or a population of implanted cells that produce the replacement protein). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can administered in these methods.

Subcutaneous injections the replacement protein and/or ASSC have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

Timing.

When the replacement protein and ASSC are in separate formulations, administration may be simultaneous, or the ASSC may be administered prior to, or after the replacement protein. For example, where the replacement protein is administered intravenously, the ASSC may be administered during a period from 0 h to 6 h later. Alternatively, the chaperone may be administered from 0 to 6 h prior to the protein.

In a preferred embodiment, where the ASSC and replacement protein are administered separately, and where the ASSC has a short circulating half-life (e.g., small molecule), the ASSC may be orally administered continuously, such as daily, in order to maintain a constant level in the circulation. Such constant level will be one that has been determined to be non-toxic to the patient, and optimal regarding interaction with a target replacement protein during the time of administration to confer a non-inhibitory, therapeutic effect.

In another embodiment, the ASSC is administered during the time period required for turnover of the replacement protein (which will be extended by administration of the ASSC).

Regardless of the timing, the administration must be such that the concentrations of the protein and ASSC must be such that the chaperone stabilizes, but does not prevent or inhibit the protein's activity in vivo. This also applies where the replacement protein and ASSC are administered in the same formulation.

In Vivo Stability.

As described above for the in vitro formulations, the presence of an ASSC for the replacement protein will have the benefit of prolonging in plasma the half-life, thereby maintaining effective replacement protein levels over longer time periods, resulting in increased exposure of clinically affected tissues to the replacement protein and, thus, increased uptake of protein into the tissues. This confers such beneficial effects to the patient as enhanced relief, reduction in the frequency, and/or reduction in the amount administered. This will also reduce the cost of treatment.

In addition to stabilizing wild-type replacement proteins, the ASSC will also stabilize and enhance expression of endogenous mutant proteins that are deficient as a result of mutations that prevent proper folding and processing in the ER, as in conformational disorders such as the LSDs.

Dosages

The amount of ASSC effective to stabilize the administered protein and endogenous mutant protein can be determined on a case-by-case basis, depending on the protein and corresponding ASSC, by those skilled in the art. Pharmacokinetics and pharmacodynamics such as half-life ($t_{1/2}$), peak plasma concentration ($c_{max}$), time to peak plasma concentration ($t_{max}$), exposure as measured by area under the curve (AUC), and tissue distribution for both the replacement protein and the ASSC, as well as data for ASSC-replacement protein binding (affinity constants, association and dissociation constants, and valency), can be obtained using ordinary methods known in the art to determine compatible amounts required to stabilize the replacement protein, without inhibiting its activity, and thus confer a therapeutic effect.

Data obtained from cell culture assay or animal studies may be used to formulate a therapeutic dosage range for use in humans and non-human animals. The dosage of compounds used in therapeutic methods of the present invention preferably lie within a range of circulating concentrations that includes the $ED_{50}$ concentration (effective for 50% of the tested population) but with little or no toxicity. The particular dosage used in any treatment may vary within this range, depending upon factors such as the particular dosage form employed, the route of administration utilized, the conditions of the individual (e.g., patient), and so forth.

A therapeutically effective dose may be initially estimated from cell culture assays and formulated in animal models to achieve a circulating concentration range that includes the $IC_{50}$. The $IC_{50}$ concentration of a compound is the concentration that achieves a half-maximal inhibition of symptoms (e.g., as determined from the cell culture assays). Appropriate dosages for use in a particular individual, for example in human patients, may then be more accurately determined using such information.

Measures of compounds in plasma may be routinely measured in an individual such as a patient by techniques such as high performance liquid chromatography (HPLC) or gas chromatography.

Toxicity and therapeutic efficacy of the composition can be determined by standard pharmaceutical procedures, for example in cell culture assays or using experimental animals to determine the $LD_{50}$ and the $ED_{50}$. The parameters $LD_{50}$ and $ED_{50}$ are well known in the art, and refer to the doses of a compound that is lethal to 50% of a population and therapeutically effective in 50% of a population, respectively. The dose ratio between toxic and therapeutic effects is referred to as the therapeutic index and may be expressed as the ratio: $LD_{50}/ED_{50}$. ASSCs that exhibit large therapeutic indices are preferred.

According to current methods, the concentration of replacement protein is between 0.05-5.0 mg/kg of body weight, typically administered weekly or biweekly. The protein can be administered at a dosage ranging from 0.1 µg/kg to about 10 mg/kg, preferably from about 0.1 mg/kg to about 2 mg/kg. For example, for the treatment of Fabry disease, the dose of recombinant α-Gal A administrated is typically between 0.1-0.3 mg/kg and is administered weekly or biweekly. Regularly repeated doses of the protein are necessary over the life of the patient. Subcutaneous injections maintain longer term systemic exposure to the drug. The subcutaneous dosage is preferably 0.1-5.0 mg of the α-Gal A per kg body weight biweekly or weekly. The α-Gal A is also administered intravenously, e.g., in an intravenous bolus injection, in a slow push intravenous injection, or by continuous intravenous injection. Continuous IV infusion (e.g., over 2-6 hours) allows the maintenance of specific levels in the blood.

The optimal concentrations of the ASSC will be determined according to the amount required to stabilize the recombinant protein in vivo, in tissue or circulation, without preventing its activity, bioavailability of the ASSC in tissue or in circulation, and metabolism of the ASSC in tissue or in circulation. For example, where the ASSC is an enzyme inhibitor, the concentration of the inhibitor can be determined by calculating the $IC_{50}$ value of the specific chaperone for the enzyme. Taking into consideration bioavailability and metabolism of the compound, concentrations around the $IC_{50}$ value or slightly over the $IC_{50}$ value can then be evaluated based on effects on enzyme activity, e.g., the amount of inhibitor needed to increase the amount of enzyme activity or prolong enzyme activity of the administered enzyme. As an example, the $IC_{50}$ value of the compound deoxygalactonojiromycin (DGJ) for the α-Gal A enzyme is 0.04 µM, indicating that DGJ is a potent inhibitor. Accordingly, it is expected that the intracellular concentration of α-Gal A would be much lower than that of the α-Gal A administered. See Examples below.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

In Vitro Stabilization of α-Gal A with ASSCs

Methods.

The wild type α-Gal A was purified from culture medium of Sf-9 cells infected with recombinant baculovirus carrying human wild type α-Gal A cDNA and the mutant α-Gal A was collected as homogenates of hearts of transgenic mice overexpressing human mutant (R301Q) α-Gal A. The mice were treated with 0.5 mM DGJ as drinking water for one week prior to the experiment. The mutant and wild type enzymes were pre-incubated with 0.1 M citrate-phosphate buffer (pH 7.0) at 37° C. for the mutant enzyme and 42° C. for the wild type enzyme, respectively, in the presence of DGJ at a concentration of 1 μM, 0.1 μM, 0.03 μM or no DGJ. The wild type and mutant (R301Q) α-Gal A were incubated for a period of time in the absence or presence of DGJ (various concentrations), and the remaining enzyme activity was determined with 4-MU-α-Gal A as a substrate, after diluting the mixture with 5-volume of 0.1 M citrate buffer (pH 4.5). Enzyme activity is reported relative to the enzyme without pre-incubation.

Results.

As shown in FIG. 1, the mutant enzyme was not stable at neutral pH after incubation at 37° C. for 20 min without incubation with DGJ (FIG. 1A). The wild type enzyme also lost significant enzyme activity at neutral pH at 42° C. without incubation with DGJ (FIG. 1B). The stability of both enzymes can be improved by inclusion of DGJ at 1 μM concentration, i.e., more than 80% of enzyme activity was remained in the reaction mixture for 60 min. This indicates that the ASSC (DGJ) can serve as a stabilizer to prevent the denaturation/degradation of the mutant and wild type enzymes.

Example 2

Intracellular Enhancement of Wild-Type α-Gal A with ASSCs

Methods.

Human wild type α-Gal A purified from insect cells transfected with recombinant baculovirus or from recombinant CHO cells can be conjugated to α-2-macroglobulin (α-2-M), according to the previous reference (Osada et al., Biochem Biophys Res Commun. 1993; 142: 100-6). Since the conjugate of α-Gal A from coffee beans and α-2-M can be internalized by cultured fibroblasts derived from Fabry hemizygotes, the conjugate of α-Gal A and α-2-M is expected to be internalized by the cells as well. Alternatively, the wild type α-Gal A can be added into the culture medium of skin fibroblasts derived from Fabry patient with no residual enzyme activity as described in Blom et al., Am J Hum Gen. 2003; 72: 23-31.

Results.

The half-life of the coffee bean α-Gal A is about 2 hr as described previously (Osada et al., Biochem Biophys Res Commun. 1987; 143: 954-8). It is expected that the half-life of the α-Gal A/α-2-M conjugate or α-Gal A added into the culture medium can be extended by inclusion of DGJ into the culture medium, since the DGJ has been shown to be effective in stabilize the enzyme in vitro (FIG. 1). This will indicate that the DGJ can prolong the exogenous α-Gal A taken up by the cells intracellularly.

Example 3

Co-Administration of DGJ to Fabry Mice Treated by Infusion of Replacement Enzyme Enzyme replacement therapy for Fabry disease has been developed by Genzyme Corporation as described above. It is expected that co-administration of DGJ to Fabry knock-out (KO) mice treated by infusion of the replacement enzyme increases the stability, e.g., half-life of the replacement enzyme in vivo, because the ASSC DGJ stabilizes the enzyme and prevents degradation. DGJ is orally administered to the KO mice after infusion of the wild type α-Gal A according to the protocol described previously (Ioannu et al., Am J Hum Genet. 2001; 68:14-25). The α-Gal A activity in various tissues including heart, kidney, spleen, liver, and lung as well as serum is determined over a period of time, and compared with those from the control mice that do not receive DGJ, and mice that receive only DGJ but no enzyme. The extended time will indicate that co-administration of ASSC can improve the efficiency of enzyme replacement therapy.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, procedures, and the like are cited throughout this application, the disclosures of which are incorporated herein by reference in their entireties.

What is claimed:

1. A method of increasing in vitro thermal stability of a purified recombinant human wild-type α-galactosidase A in a formulation having a pH greater than 5.0 suitable for parenteral administration to a human, the method comprising contacting the purified recombinant human wild-type α-galactosidase A in a pharmaceutically acceptable carrier having a pH greater than 5.0 with an amount of 1-deoxygalactonojirimycin effective to increase the in vitro stability of the purified recombinant human wild-type α-galactosidase A, and pre-incubating the purified recombinant human wild-type α-galactosidase A in a pharmaceutically acceptable carrier having a pH greater than 5.0 with an amount of 1-deoxygalactonojirimycin effective to increase the in vitro stability of the purified recombinant human wild-type α-galactosidase A at a temperature from 37° C. to 42° C. for sixty (60) minutes;
   wherein the formulation is a sterile injectable solution retaining more than 80% of the enzyme activity of human wild-type α-galactosidase A after said pre-incubation.

2. The method of claim 1, wherein the formulation has a neutral pH.

3. The method of claim 1, wherein the in vitro thermal stability is stability at a temperature of 42° C.

4. A method of increasing in vitro thermal stability of a purified recombinant human wild-type α-galactosidase A in a sterile injectable solution formulation having a pH of about 7.0-7.5 suitable for parenteral administration to a human, the method comprising contacting the purified recombinant human wild-type α-galactosidase A in a pharmaceutically acceptable carrier having a pH of about 7.0-7.5 with an amount of 1-deoxygalactonojirimycin effective to increase the in vitro thermal stability of the purified recombinant human wild-type α-galactosidase A and pre-incubating the purified recombinant human wild-type α-galactosidase A in a pharmaceutically acceptable carrier having a pH of about 7.0-7.5 with an amount of 1-deoxygalactonojirimycin effective to increase the in vitro stability of the purified recombinant human wild-type α-galactosidase A at a temperature from 37° C. to 42° C. for sixty (60) minutes prior;
    wherein the formulation retains more than 80% of the enzyme activity of human wild-type α-galactosidase A after said pre-incubation.

\* \* \* \* \*